(12) United States Patent
Garcia Molina et al.

(10) Patent No.: US 11,433,214 B2
(45) Date of Patent: Sep. 6, 2022

(54) SYSTEM AND METHOD TO SHORTEN SLEEP LATENCY

(71) Applicant: KONINKLIJKE PHILIPS N.V., Eindhoven (NL)

(72) Inventors: Gary Nelson Garcia Molina, Madison, WI (US); Boomika Kalyan, Pittsburgh, PA (US); Antonio Aquino, Harrison City, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/111,791

(22) Filed: Dec. 4, 2020

(65) Prior Publication Data

US 2021/0170137 A1    Jun. 10, 2021

Related U.S. Application Data

(60) Provisional application No. 62/945,522, filed on Dec. 9, 2019.

(51) Int. Cl.
*A61M 21/00*    (2006.01)

(52) U.S. Cl.
CPC ..... *A61M 21/00* (2013.01); *A61M 2021/0022* (2013.01); *A61M 2021/0027* (2013.01);
(Continued)

(58) Field of Classification Search
CPC ............. A61M 21/00–02; A61B 5/4806–4815
See application file for complete search history.

(56) References Cited

U.S. PATENT DOCUMENTS

| | | |
|---|---|---|
| 9,993,610 B2 | 6/2018 | Garcia Molina |
| 2010/0056941 A1 | 3/2010 | Henke et al. |

(Continued)

FOREIGN PATENT DOCUMENTS

| | | |
|---|---|---|
| EP | 3181041 A1 | 6/2017 |
| JP | 2005342468 A | 12/2005 |

(Continued)

OTHER PUBLICATIONS

Bresch, E. et al., "Recurrent Deep Neural Networks for Real-Time Sleep Stage Classification From Single Channel EEG", Front. Comput. Neurosci., Oct. 16, 2018.

(Continued)

*Primary Examiner* — Thaddeus B Cox

(57) ABSTRACT

The present disclosure pertains to shortening sleep latency during the wake to sleep transition. Sensory stimulation is delivered to a subject by sensory stimulators during a sleep session, and a measure of wakefulness of the subject is determined. The sensory stimulators are controlled based on the measure of wakefulness of the subject. The sensory stimulators may be controlled to modulate an intensity of the sensory stimulation delivered to the subject. For example, the sensory stimulators may decrease the intensity of the sensory stimulation as the measure of wakefulness decreases. The system then determines that the measure of wakefulness has reached stable sleep. The sensory stimulators are controlled based on the determination that the measure of wakefulness has reached stable sleep. The sensory stimulators may decrease the intensity of the sensory stimulation at a faster rate once the measure of wakefulness reaches stable sleep.

16 Claims, 7 Drawing Sheets

(52) U.S. Cl.
CPC .............. *A61M 2021/0044* (2013.01); *A61M 2021/0055* (2013.01); *A61M 2205/3327* (2013.01); *A61M 2205/42* (2013.01); *A61M 2230/10* (2013.01)

(56) References Cited

U.S. PATENT DOCUMENTS

| | | |
|---|---|---|
| 2014/0057232 A1 | 2/2014 | Anderson |
| 2016/0151602 A1* | 6/2016 | Pan ..................... A61B 5/4836 600/28 |
| 2016/0296164 A1* | 10/2016 | Garcia Molina .... A61B 5/7278 |
| 2018/0361110 A1* | 12/2018 | Garcia Molina ...... A61B 5/291 |
| 2019/0143073 A1* | 5/2019 | Grossman ............. A61M 21/02 600/28 |
| 2019/0298967 A1* | 10/2019 | Garcia Molina ..... A61M 21/02 |

FOREIGN PATENT DOCUMENTS

| | | |
|---|---|---|
| JP | 2009039339 A | 2/2009 |
| WO | 2005055802 A2 | 6/2005 |
| WO | 2015087188 A1 | 6/2015 |
| WO | 2015118415 A1 | 8/2015 |
| WO | 2016011804 A1 | 1/2016 |
| WO | 2017109621 A1 | 6/2017 |
| WO | 2018104309 A1 | 6/2018 |
| WO | 2019115412 A1 | 6/2019 |

OTHER PUBLICATIONS

Borbély, A. A. (1982) 'A two process model of sleep regulation.', Human Neurobiology. Human Neurobiol, 1(3), pp. 195-204.

Carskadon, M. A. and Dement, W. C. (2011) 'Normal human sleep: an overview', in Kryger, M. H., Roth, T., and Dement, W.C. (eds) Principles and practice of sleep medicine. 5th edn. Elsevier, pp. 16-26.

Chouchou, F. and Desseilles, M. (2014) 'Heart rate variability: a tool to explore the sleeping brain?', Autonomic Neuroscience, Dec. 8, pp. 1-9. doi: 10.3389/fnins.2014.00402.

Hori, T., Hayashi, M. and Morikawa, T. (1993) 'Topographical EEG changes and hypnagogic experience', in Ogilvie, R. D. and Harsh, J. R. (eds) Sleep Onset: Normal and Abnormal Processes, pp. 237-253.

Radha, M. et al. (2014) 'Comparison of Feature and Classifier Algorithms for Online Automatic Sleep Staging Based on a Single EEG Signal', in 36th Annual International Conference of the IEEE Engineering in Medicine and Biology Society (EMBC), pp. 1876-1880.

Schütze, M. D. and Junghanns, K. (2015) 'The Difficulty of Staying Awake During Alpha/Theta Neurofeedback Training', Applied Psychophysiology and Biofeedback, pp. 85-94. doi: 10.1007/s10484-015-9278-9.

Zhang, Z. et al. (2015) 'Reduction in time-to-sleep through EEG based brain state detection and audio stimulation', Proceedings of the Annual International Conference of the IEEE Engineering in Medicine and Biology Society, EMBS. IEEE, 2015—Novem, pp. 8050-8053. doi: 10.1109/EMBC.2015.7320261.

Zhao, M. et al. (2017) 'Learning Sleep Stages from Radio Signals: A Conditional Adversarial Architecture', in 34th International Conference on Machine Learning, pp. 4100-4109. Available at: http://proceedings.mlr.press/v70/zhao17d.html.

International Search Report and Written Opinion, International Application No. PCT/EP2020/083993, dated Mar. 3, 2021.

\* cited by examiner

SYSTEM AND METHOD TO SHORTEN SLEEP LATENCY

CROSS-REFERENCE TO PRIOR APPLICATIONS

This application claims the benefit of U.S. Provisional Application No. 62/945,522, filed on 9 Dec. 2019. This application is hereby incorporated by reference herein.

BACKGROUND

1. Field

The present disclosure pertains to a system and method for controlling sensory stimulation delivered to a subject during a sleep session.

2. Description of the Related Art

Systems for monitoring sleep and delivering sensory stimulation to subjects during sleep are known. Electroencephalogram (EEG) sensor-based sleep monitoring and sensory stimulation systems are known.

SUMMARY

It would be advantageous to shorten sleep latency of a subject during a wake to sleep transition of a sleep session. Delivery of modulated sensory stimulation to a subject may induce sleep onset and shorten sleep latency. Accordingly, one or more aspects of the present disclosure relate to a system configured to control sensory stimulation delivered to a subject during a sleep session. The system comprises one or more sensors, one or more sensory stimulators, one or more processors, and/or other components. The one or more sensors are configured to generate output signals conveying information related to brain activity of the subject during the sleep session. The one or more sensory stimulators are configured to provide the sensory stimulation to the subject during the sleep session. The one or more processors are coupled to the one or more sensors and the one or more sensory stimulators. The one or more processors are configured by machine-readable instructions. The one or more processors are configured to control the one or more sensory stimulators based on stimulation parameters.

In some embodiments, the one or more sensors comprise one or more electroencephalogram (EEG) electrodes configured to generate the information related to brain activity. In some embodiments, the one or more processors are further configured to detect a measure of wakefulness of the subject. The measure of wakefulness may comprise a quantitative assessment of a subject's brain activity. In some embodiments, the measure of wakefulness (e.g., based on the brain activity of the subject during the sleep session) may indicate a degree of wakefulness or a degree of sleepiness. In some embodiments, the measure of wakefulness may comprise a probability of wake versus a probability of a sleep stage (e.g., using sleep stage probability outputs from a neural network). In some embodiments, the measure of wakefulness may comprise a ratio of a high frequency portion of the brain signals to a low frequency portion of the brain signals. In some embodiments, measure of wakefulness may comprise a power ratio of a power associated with a high frequency portion of the brain signals to a power associated with a low frequency portion of the brain signals. In some embodiments, the measure of wakefulness may comprise a sleep stage during the subject's sleep session. In some embodiments, the measure of wakefulness may comprise a measure of heart rate ruing the wake to sleep transition (e.g., heart rate tends to be higher during wake than during sleep). In some embodiments, the measure of wakefulness may comprise a measure of heart rate variability (e.g., heart rate variability is the standard deviation of successive hear beats within a time period and tends to be lower during wake than during sleep. In some embodiments, the measure of wakefulness may comprise another assessment of the subject's brain activity. Wakefulness may comprise any of the aforementioned definitions, and the present disclosure broadly contemplates these and/or other definitions in the art.

In some embodiments, the one or more processors are further configured to detect when the subject has entered stable sleep. In some embodiments, stable sleep may comprise uninterrupted non-rapid eye movement (NREM) sleep (which includes stages N1, N2 and N3 or S1 to S4 according to the old nomenclature). In some other embodiments, stable sleep corresponds to an uninterrupted period of rapid eye movement (REM). Stable sleep may comprise either of the aforementioned definitions, and the present disclosure broadly contemplates these and/or other definitions in the art. In some embodiments, the one or more processors are configured to determine that the subject has remained in NREM or REM sleep for a continuous threshold amount of time during the sleep session.

In some embodiments, detecting the measure of wakefulness and sleep stage comprises causing a neural network to be trained based on the information related to the brain activity of the subject, as captured by the EEG electrodes. In some embodiments, an intermediate output of the neural network may be probabilities that a subject is in various sleep stages. In some embodiments, a measure of wakefulness may be calculated as a ratio of the probability of the wake stage versus the probably of the NREM stage. In some embodiments, based on the output signals, the trained neural network may determine a measure of wakefulness of the subject throughout the sleep session as well as periods when the subject is experiencing NREM or REM sleep during the sleep session. The trained neural network comprises an input layer, an output layer, and one or more intermediate layers between the input layer and the output layer.

In some embodiments, the one or more processors are configured to control the one or more sensory stimulators according to the measure of wakefulness of the subject. In some embodiments, controlling the sensors may comprise modulating the sensory stimulation such that the intensity of the sensory stimulation is proportional to the measure of wakefulness. In this embodiment, as measure of wakefulness decreases (i.e., the user falls asleep), the intensity of the sensory stimulation will decrease accordingly. In some embodiments, the decreasing intensity of the sensory stimulation may cause the brain activity of the subject to match the decreasing trend of the sensory stimulation, thereby facilitating sleep onset. In some embodiments, if the measure of wake of wakefulness increases or stays constant, the one or more processors may control the one or more sensory stimulators to deliver the sensory stimulation to the subject at a constant intensity. These control parameters are not intended to be limiting.

In some embodiments, the one or more processors are configured such that, once stable NREM or REM sleep is detected, the processors control the sensory stimulators to decrease the intensity of the sensory stimulation at a faster rate than at higher measures of wakefulness. In some embodiments, this may comprise fading the intensity of the sensory stimulation to zero. In some embodiments, this may comprise fading the intensity until the intensity is below a perceivable threshold, at which point the intensity is set to zero. In some embodiments, the one or more sensory stimulators are configured such that the sensory stimulation comprises audible tones. In some embodiments, the one or more sensory stimulators are configured such that the sensory stimulation comprises haptic vibrations. In some embodiments, the one or more sensory stimulators are configured such that the sensory stimulation comprises light pulses.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
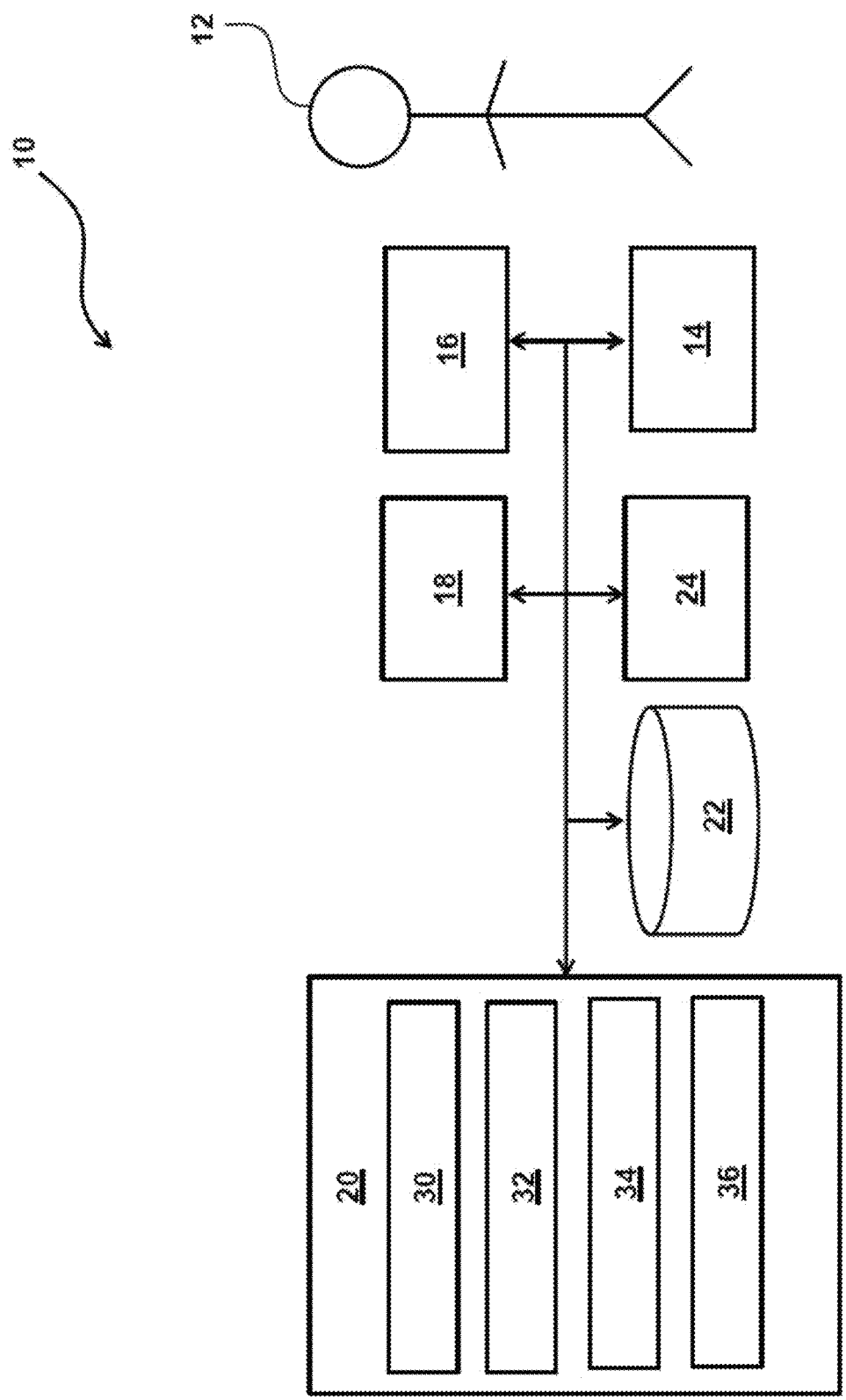
FIG. 1 is a schematic illustration of a system configured to deliver sensory stimulation to a subject during a sleep session, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to deliver sensory stimulation to a subject 12 during a sleep session. System 10 is configured to facilitate delivery of sensory stimulation to subject 12 to determine if subject 12 responds to sensory stimulation, to update stimulation parameters, and/or for other purposes. System 10 is configured such that sensory stimulation including auditory, haptic, visual, and/or other stimulation is delivered before and/or during sleep. In some embodiments, the stimulation is modulated according to a measure of wakefulness of the subject 12. In some embodiments, the stimulation is modulated differently when processors in system 10 (described below) have determined that the subject 12 is in stable sleep. In some embodiments, system 10 delivers stimulation to subject 12 with a modulated intensity (e.g., volume of auditory tones, strength of haptic vibrations, brightness of light pulses, and/or another intensity for the stimulations). As described herein, the one or more processors may control the sensory stimulators to modulate the intensity of the stimulation such that the intensity is proportional to a measure of wakefulness of the subject. Accordingly, as the subject falls asleep, the intensity of the sensory stimulation decreases. In some embodiments, if the measure of wakefulness increases or remains constant, the intensity of the sensory stimulation may remain constant. In some embodiments, once stable sleep is detected, the one or more processors may control the sensory stimulators to decrease the intensity of the sensory stimulation at a faster rate than at higher measures of wakefulness.

Modulating stimulation delivered to a subject during the wake to sleep transition parameters is important to reducing sleep latency of the subject. The modulated stimulation assists the subject's process of falling asleep and is customized to the sleep architecture of the subject during the sleep session. System 10 also leverages machine-learning models (e.g., deep neural networks and/or any other supervised machine learning algorithm as described below) for automatic, real-time or near real-time, closed loop, sensor output signals for determining the measure of wakefulness and the sleep stages of the subject during the sleep session. As shown in FIG. 1, system 10 includes one or more of a sensor 14, a sensory stimulator 16, external resources 18, a processor 20, electronic storage 22, a subject interface 24, and/or other components. These components are further described below.

Sensor 14 is configured to generate output signals conveying information related to sleep stages of subject 12 during a sleep session. The output signals conveying information related to sleep stages of subject 12 may include information related to brain activity in subject 12. As such, sensor 14 is configured to generate output signals conveying information related to brain activity. In some embodiments, sensor 14 is configured to generate output signals conveying information related to stimulation provided to subject 12 during sleep sessions. In some embodiments, the information in the output signals from sensor 14 is used to control sensory stimulator 16 to provide sensory stimulation to subject 12 (as described below).

Sensor 14 may comprise one or more sensors that generate output signals that convey information related to brain activity in subject 12 directly. For example, sensor 14 may include electroencephalogram (EEG) electrodes configured to detect electrical activity along the scalp of subject 12 resulting from current flows within the brain of subject 12.

Sensor 14 may comprise one or more sensors that generate output signals conveying information related to brain activity of subject 12 indirectly. For example, one or more sensors 14 may comprise a heart rate sensor that generates an output based on a heart rate of subject 12 (e.g., sensor 14 may be a heart rate sensor than can be located on the chest of subject 12, and/or be configured as a bracelet on a wrist of subject 12, and/or be located on another limb of subject 12), movement of subject 12 (e.g., sensor 14 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, sensor 14 may comprise one or more of EEG electrodes, a respiration sensor, a pressure sensor, a vital signs camera, a functional near infra-red sensor (fNIR), a temperature sensor, a microphone and/or other sensors configured to generate output signals related to (e.g., the quantity, frequency, intensity, and/or other characteristics of) the stimulation provided to subject 12, the brain activity of subject 12, and/or other sensors. Although sensor 14 is illustrated at a single location near subject 12, this is not intended to be limiting. Sensor 14 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Figure 2:
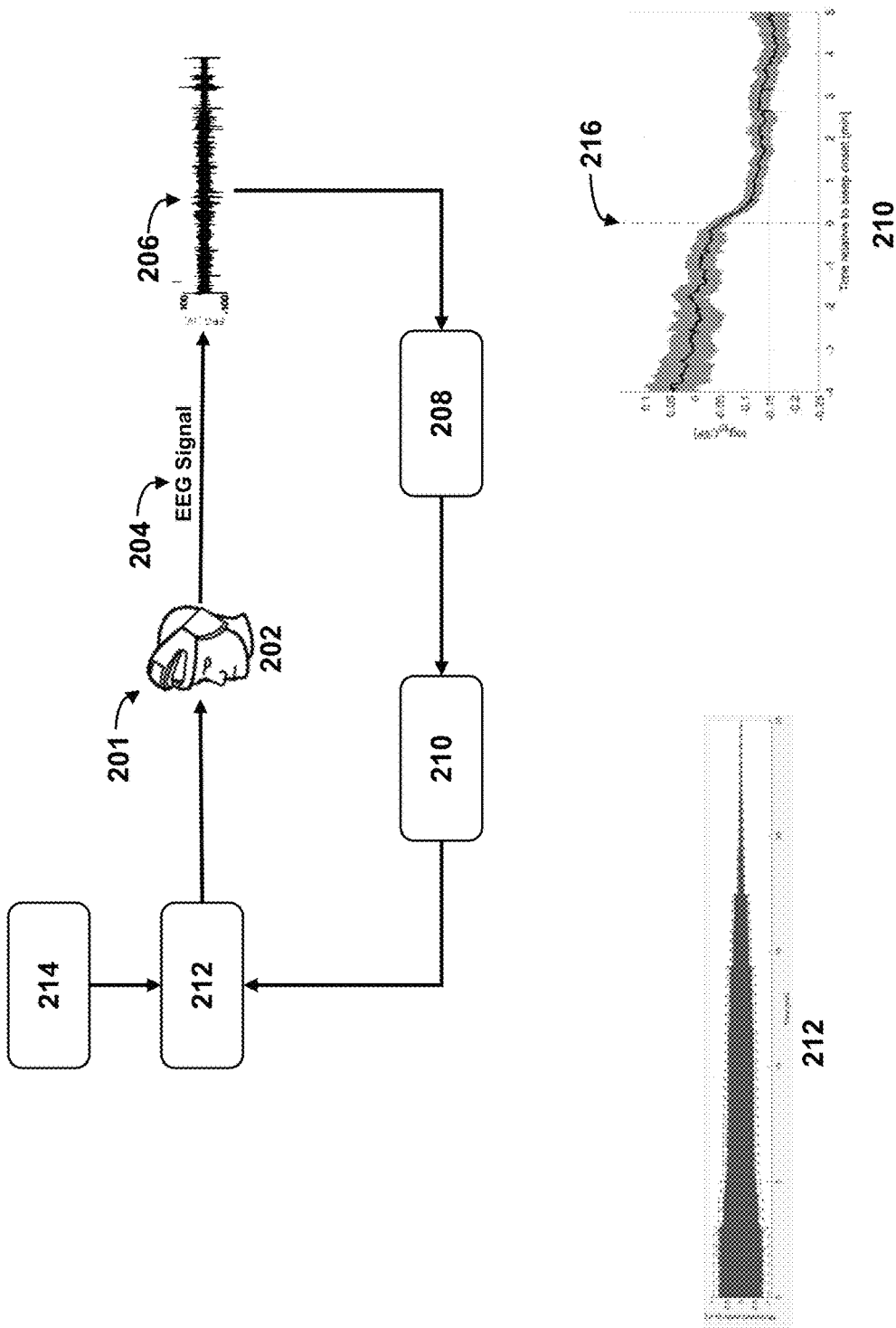
FIG. 2 illustrates several of the operations performed by the system, in accordance with one or more embodiments.

In FIG. 1, sensor 14, sensory stimulator 16, processor 20, electronic storage 22, and subject interface 24 are shown as separate entities. This is not intended to be limiting. Some and/or all of the components of system 10 and/or other components may be grouped into one or more singular devices. For example, these and/or other components may be included in a wearable device 201. In some embodiments, wearable device 201 may be a headset as illustrated in FIG. 2 and/or other garments worn by subject 12. Other garments may include a cap, vest, bracelet, and/or other garment. In some embodiments, wearable device 201 may comprise one or more sensors which may contact the skin of the subject. In some embodiments, wearable device 201 may comprise one or more sensory stimulators, which may provide auditory vibrations, haptic vibrations, light pulses, and/or other stimulation. For example, wearable device 201 and/or other garments may include, for example, sensing electrodes, a reference electrode, one or more devices associated with an EEG, means to deliver auditory stimulation (e.g., a wired and/or wireless audio device and/or other devices), and one or more audio speakers. In some embodiments, wearable device 201 may comprise means to delivery visual, somatosensory, electric, magnetic, and/or other stimulation to the subject. In this example, the audio speakers may be located in and/or near the ears of subject 12 and/or in other locations. The reference electrode may be located behind the ear of subject 12, and/or in other locations. In this example, the sensing electrodes may be configured to generate output signals conveying information related to brain activity of subject 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to subject 12 via the wireless audio device and/or speakers. In this example, the sensing electrodes, the reference electrode, and the EEG devices may be represented, for example, by sensor 14 in FIG. 1. The wireless audio device and the speakers may be represented, for example, by sensory stimulator 16 shown in FIG. 1. In this example, a computing device may include processor 20, electronic storage 22, subject interface 24, and/or other components of system 10 shown in FIG. 1.

Sensory stimulator 16 is configured to provide sensory stimulation to subject 12. Sensory stimulator 16 is configured to provide auditory, visual, somatosensory, electric, magnetic, and/or sensory stimulation to subject 12 prior to a sleep session, during a wake to sleep transition, during a sleep session, and/or at other times. In some embodiments, a sleep session may comprise any period of time when subject 12 is sleeping and/or attempting to sleep. Sleep sessions may include nights of sleep, naps, and/or other sleeps sessions. In some embodiments, the system may identify a sleep session through observation of the subject (e.g., via camera, light detection, etc.). For example, if the subject lies down, turns off the lights in a room that the subject is in, and/or lies still for certain amount of time, the system may identify that a sleep session has begun. In some embodiments, the system may identify that a sleep session has begun with the subject switches on a sleep device (e.g., a Philips SmartSleep device). For example, sensory stimulator 16 may be configured to provide stimuli to subject 12 during a sleep session to enhance EEG signals during NREM or REM sleep in subject 12, and/or for other purposes.

Sensory stimulator 16 is configured to affect the wake to sleep transition and stable sleep of subject 12 through non-invasive brain stimulation and/or other methods. Sensory stimulator 16 may be configured to affect sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, stimulation may be provided to subject 12 to affect sleep in subject 12. The stimulation may comprise a continuous stimulation delivered to the subject. The acoustic tones may include one or more series of stimulations of a determined length separated from each other by an inter-stimulation interval. The intensity (e.g., the volume) of the stimulation may be modulated based on various factors (as described herein). The pitch and tone may also be adjusted. In some embodiments, the intensity of the stimulation is modulated according to the measure of wakefulness of the subject. For example, if the stimulation is auditory, the subject may set the initial volume of the stimulation. The intensity of the auditory stimulation may decrease as the measure of wakefulness of the subject decreases during the wake to sleep transition. In some embodiments, once the subject reaches stable sleep, the volume of the auditory stimulation may fade to zero. This example is not intended to be limiting, and the stimulation modulation parameters may vary.

Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual subjects, and/or other resources. In some implementations, some or all of the functionality attributed herein to external resources 18 may be provided by resources included in system 10. External resources 18 may be configured to communicate with processor 20, subject interface 24, sensor 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, subject interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical subject interfaces configured to facilitate subject interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a modulation component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to determine one or more brain activity parameters of subject 12, and/or other information. The brain activity parameters are determined based on the output signals from sensor 14 and/or other information. The brain activity parameters indicate measure of wakefulness in subject 12. In some embodiments, the information in the output signals related to brain activity indicates measure of wakefulness over time. In some embodiments, the information indicating measure of wakefulness over time is or includes information related to the wake to sleep transition and/or stable sleep of subject 12.

In some embodiments, the information indicating measure of wakefulness over time may be indicative of sleep stages of subject 12. For example, the sleep stages of subject 12 may be associated with NREM or REM sleep, rapid eye movement (REM) sleep, and/or other sleep. NREM sleep may be stage N3, and/or other sleep stages. In some embodiments, the sleep stages of subject 12 may be one or more of stage S1, S2, S3, or S4. In some embodiments, NREM stage 2 and/or 3 (and/or S3 and/or S4) may be slow wave (e.g., deep) sleep. In some embodiments, initiation of sleep through the REM stage may be indicative of a sleeping disorder. In some embodiments, the information that indicates measure of wakefulness over time is and/or is related to one or more additional brain activity parameters.

In some embodiments, the information related to brain activity that indicates measure of wakefulness over time is and/or includes EEG information and/or other information generated during sleep sessions of subject 12 and/or at other times. In some embodiments, brain activity parameters may be determined based on the EEG information and/or other information. In some embodiments, the brain activity parameters may be determined by information component 30 and/or other components of system 10. In some embodiments, the brain activity parameters may be previously determined and be part of the historical sleep stage information obtained from external resources 18 (described below). In some embodiments, the one or more brain activity parameters are and/or are related to a frequency, amplitude, phase, presence of specific sleep patterns such as eye movements, ponto-geniculo-occipital (PGO) wave, slow wave, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate a measure of wakefulness and/or sleep stages that correspond to stable sleep.

Information component 30 is configured to obtain historical sleep stage information. In some embodiments, the historical sleep stage information is for subject 12 and/or other subjects. The historical sleep stage information is related to brain activity, and/or other physiological of the population of subjects and/or subject 12 that indicates measure of wakefulness and sleep stages over time during previous sleep sessions of subject 12 and/or other subjects. The historical sleep stage information is related to sleep stages and/or other brain parameters of subject 12 and/or other subjects during corresponding sleep sessions, and/or other information.

In some embodiments, information component 30 is configured to obtain the historical sleep stage information electronically from external resources 18, electronic storage 22, and/or other sources of information. In some embodiments, obtaining the historical sleep stage information electronically from external resources 18, electronic storage 22, and/or other sources of information comprises querying one more databases and/or servers; uploading information and/or downloading information, facilitating subject input, sending and/or receiving emails, sending and/or receiving text messages, and/or sending and/or receiving other communications, and/or other obtaining operations. In some embodiments, information component 30 is configured to aggregate information from various sources (e.g., one or more of the external resources 18 described above, electronic storage 22, etc.), arrange the information in one or more electronic databases (e.g., electronic storage 22, and/or other electronic databases), normalize the information based on one or more features of the historical sleep stage information (e.g., length of sleep sessions, number of sleep sessions, etc.) and/or perform other operations.

Model component 32 is configured such that a trained neural network and/or any other supervised machine learning algorithms are caused to detect a measure of wakefulness and/or stable sleep in subject 12. In some embodiments, this may be and/or include determining periods when subject 12 is experiencing a wake to sleep transition and/or stable sleep (e.g., five minutes of uninterrupted NREM or REM sleep) during the sleep session and/or other operations. By way of a non-limiting example, a trained neural network may be caused to indicate determine the wake to sleep transition, a measure of wakefulness, stable sleep stages, and/or timing of the aforementioned sleep events of the subject based on the output signals (e.g., using the information in the output signals as input for the model) and/or other information. In some embodiments, model component 32 is configured to provide the information in the output signals to the neural network in temporal sets that correspond to individual periods during the sleep session. In some embodiments, model component 32 is configured to cause the trained neural network to output the determined measure of wakefulness, sleep stages, and/or stable sleep of subject 12 during the sleep session based on the temporal sets of information. (The functionality of model component 32 is further discussed below relative to FIG. 2-3). In some embodiments, model component 32 is or includes the trained neural network.

Neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function that combines the values of all its inputs together. In some embodiments, each connection (or the neural unit itself) may have a threshold function such that a signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

A trained neural network may comprise one or more intermediate or hidden layers. The intermediate layers of the trained neural network include one or more convolutional layers, one or more recurrent layers, and/or other layers of the trained neural network. Individual intermediate layers receive information from another layer as input and generate corresponding outputs. The detected measure of wakefulness, sleep stages, and/or stable sleep are generated based on the information in the output signals from sensor 14 as processed by the layers of the neural network.

Control component 34 is configured to control stimulator 16 to provide stimulation to subject 12 during sleep and/or at other times. Control component 34 is configured to cause sensory stimulator 16 to provide modulated sensory stimulation to subject 12 during a sleep session. In some embodiments, control component 34 is configured to cause sensory stimulator 16 to modulate the sensory stimulation delivered to subject 12 based on a detected measure of wakefulness (e.g., the output from model component 32) and/or other information. In some embodiments, control component 34 is configured to cause sensory stimulator 16 to modulate the sensory stimulation to subject 12 based on detected stable sleep and/or other information over time during the sleep session. Control component 34 is configured to cause sensory stimulator 16 to modulate the intensity sensory stimulation to subject 12 responsive to a decrease in a measure of wakefulness of subject 12. For example, control component 34 is configured such that controlling one or more sensory stimulators 16 to modulate the sensory stimulation to subject 12 during the sleep session comprises: determining a measure of wakefulness of the subject during the sleep session, controlling the sensory stimulation delivered to the subject based on the measure of wakefulness, determining that the measure of wakefulness has reached stable sleep, and controlling the sensory stimulation delivered to the subject based on the stable sleep. In some embodiments, stimulators 16 are controlled by control component 34 to affect the wake to sleep transition through (e.g., auditory, haptic, visual, and/or other) stimulation delivered during the sleep session (as described herein).

In some embodiments, control component 34 is configured to control sensory stimulator 16 to modulate an intensity of the sensory stimulation delivered to subject 12 responsive to model component 32 determining that the measure of wakefulness of the subject has remained in stable sleep for a continuous threshold amount of time during the sleep session. For example, model component 32 and/or control component 34 may be configured such that on detection of stable sleep, model component 32 starts a (physical or virtual) timer configured to track the time subject 12 spends in stable sleep. Control component 34 is configured to modulate stimulation responsive to the duration that subject 12 spends in continuous stable sleep breaching a predefined duration threshold. In some embodiments, the predefined duration threshold is determined at manufacture of system 10 and/or at other times. In some embodiments, the predefined duration threshold is determined based on information from previous sleep sessions of subject 12 and/or subjects demographically similar to subject 12 (e.g., as described above). In some embodiments, the predefined duration threshold is adjustable via subject interface 24 and/or other adjustment mechanisms.

In some embodiments, the predefined stable sleep duration threshold may be five minutes and/or other durations, for example. By way of a non-limiting example, control component 34 may be configured such that auditory stimulation starts once five minutes of continuous stable sleep in subject 12 are detected. In some embodiments, once the stimulation begins, control component 34 is configured to control stimulation parameters of the stimulation. Upon detection of a sleep stage transition (e.g., from stable sleep to some other sleep stage), control component 34 is configured to deliver the stimulation at a constant intensity.

Modulation component 36 is configured to cause sensory stimulator 16 to modulate an amount, a timing, and/or intensity of the sensory stimulation. Modulation component 36 is configured to cause sensory stimulator 16 to modulate the amount, timing, and/or intensity of the sensory stimulation based on the brain activity parameters, values output from the intermediate layers of the trained neural network, and/or other information. As an example, sensory stimulator 16 is caused to modulate the timing and/or intensity of the sensory stimulation based on the brain activity parameters, the values output from the convolutional layers, the values output from the recurrent layers, and/or other information. For example, modulation component 36 may be configured such that sensory stimulation is delivered with an intensity that is proportional to a detected measure of wakefulness of subject 12 during the sleep session. In this example, decreases in the measure of wakefulness cause the modulation component 36 to decrease the intensity of the stimulation delivered to subject 12. If sleep micro-arousals are detected and the subject remains in stable sleep, modulation component 36 may be configured such that the intensity of the stimulation continues to fade to zero.

By way of a non-limiting example, FIG. 2 illustrates several of the operations performed by system 10 and described above. In the example shown in process 200 of FIG. 2, an EEG signal 204 of subject 202 is processed (e.g., by information component 30 and model component 32 shown in FIG. 1) in temporal window 206. In some embodiments, temporal window 206 may comprise six-second increments of EEG signal 204. In some embodiments, EEG signal 204 may be processed by a deep neural network. A deep neural network may determine sleep depth and stage information of the subject (as described below in relation to FIG. 3). In some embodiments, methods described in the publication "Recurrent Deep Neural Networks for Real-Time Sleep Stage Classification From Single Channel EEG." *Frontiers in Computational Neuroscience*. Bresch, E., Großekathöfer, U., and Garcia-Molina, G. (2018), which is hereby incorporated by reference in its entirety, may be utilized.

As shown in FIG. 2, process 200 may extract the EEG power 208 from temporal window 206. The extracted EEG power may comprise a high frequency portion and a low frequency portion of the signal of EEG signal 204 for a period of time captured in temporal window 206. In some embodiments, process 200 may calculate a ratio 210 of the high frequency portion of the signal to the low frequency portion of the signal. In some embodiments, ratio 210 may be a power ratio of a power associated with a high frequency portion of the brain signals to a power associated with a low frequency portion of the brain signals. In some embodiments, the high frequency portion of the signal may comprise a signal in the beta band (i.e., $\beta$). of the EEG signal. In some embodiments, the low frequency portion of the signal may comprise a signal in the theta band (i.e., $\theta$) of the EEG signal. In some embodiments, process 200 may additionally calculate a logarithm of ratio 210. Ratio 210 is shown in FIG. 2 as a graph of logarithm of ratio 210 based on the time relative to sleep onset 216. The logarithm of ratio 210 decreases with time. In some embodiments, the logarithm of ratio 210 may represent a measure of wakefulness of the subject throughout a sleep session. This example is not intended to be limiting. A ratio between any high frequency portion of the EEG signal and any low frequency portion of the EEG signal may be acceptable. In some embodiments, the ratio may not comprise the logarithm of the ratio.

Process 200 may then deliver modulated sensory stimulation 212 to the subject during the sleep session. In some embodiments, the modulated sensory stimulation 212 may comprise delivering sensory stimulation to the subject at a varying intensity. In some embodiments, the intensity of modulated sensory stimulation 212 may depend, in real time or near real time, on ratio 210 (e.g., the measure of wakefulness based on EEG signal 204). In some embodiments, the intensity of modulated sensory stimulation 212 may be proportional to ratio 210 and/or the logarithm of ratio 210. As shown in FIG. 2, the intensity of modulated sensory stimulation 212 may decrease as time progresses. The rate of change of the decreasing intensity may depend on the measure of wakefulness of the subject. In some embodiments, the rate of change may vary over time, leading to a decrease in intensity that is not constant (e.g., as described in related to FIG. 4). In some embodiments, once the measure of wakefulness reaches stable sleep, the intensity of modulated sensory stimulation 212 may fade to zero. In some embodiments, modulated sensory stimulation 212 may comprise any type of sensory stimulation 214, such as auditory, haptic, visual, and/or other stimulation. In some embodiments, the subject may set an initial intensity of sensory stimulation 214. In this example, process 200 may provide modulated sensory stimulation 212 once the subject beings to fall asleep and may deliver modulated sensory stimulation 212 to the subject thereafter.

Figure 3:
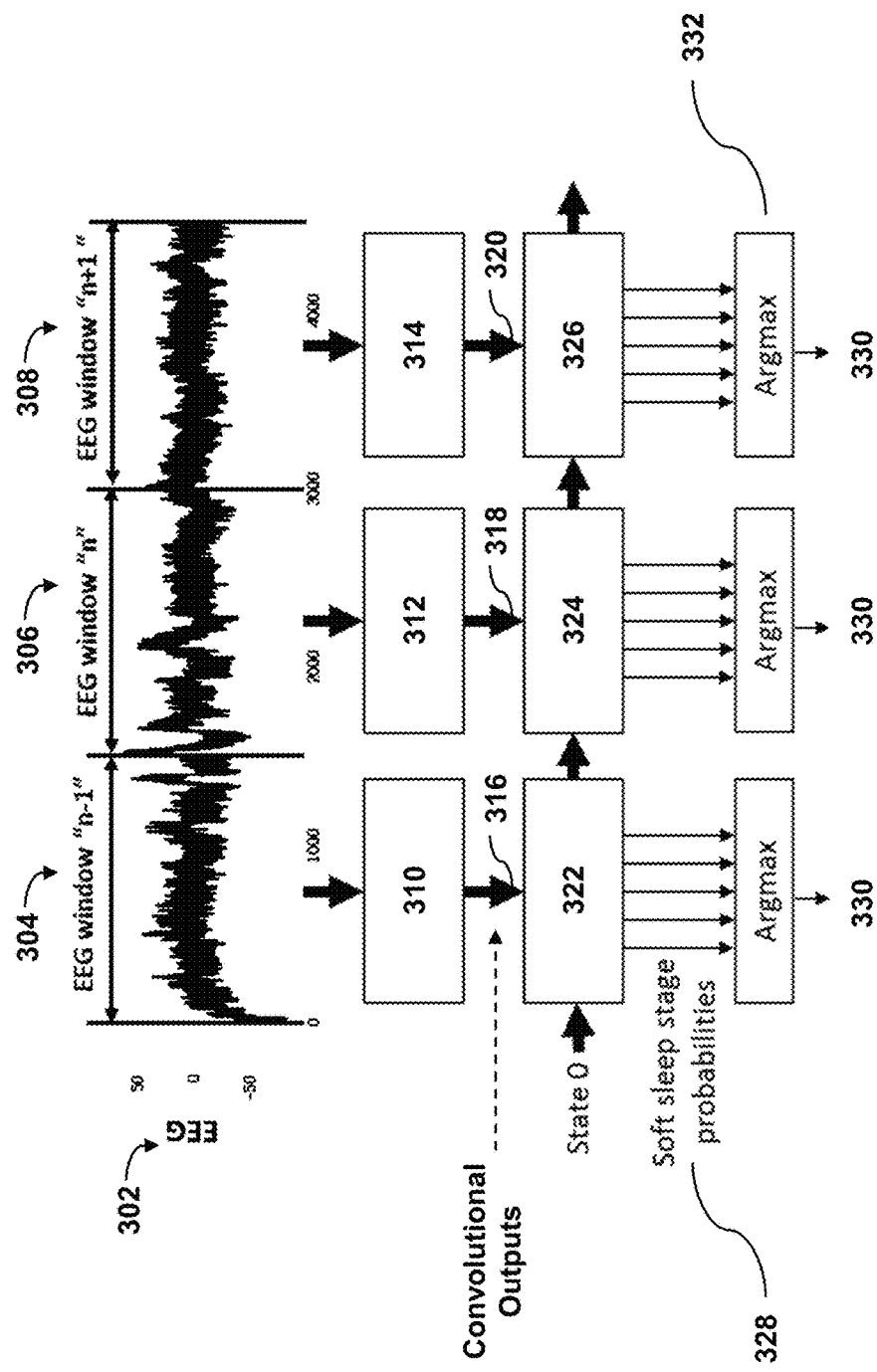
FIG. 3 illustrates example architecture of a deep neural network that is part of the system, in accordance with one or more embodiments.

FIG. 3 illustrates example architecture 300 of a deep neural network (e.g., for processing temporal window 206, as shown in FIG. 2) that is part of system 10 (FIGS. 1 and 2). FIG. 3 illustrates deep neural network architecture 300 for three (unrolled) EEG windows 304, 306, and 308. In some embodiments, windows 304, 306, and 308 may be windows of an EEG signal 302 for pre-defined time periods (e.g., six seconds). Architecture 300 includes convolutional layers 310, 312, and 314, and recurrent layers 322, 324, and 326. As described above, convolutional layers 310, 312, and 314 can be thought of as filters and produce convolution outputs 316, 318, and 320 that are fed to recurrent layers 322, 324, and 326 (LSTM (long short term memory) layers in this example). The output of architecture 300 for individual windows 304, 306, and 308 that are processed are a set of prediction probabilities for individual sleep stages, which are termed "soft output(s)" 328. "Hard" predictions 330 are determined by architecture 300 (model component 32 shown in FIG. 1) by predicting 332 a sleep stage associated with a "soft" output with the highest value (e.g., as described below). The terms "soft" and "hard" are not intended to be limiting but may be helpful to use to describe the operations performed by the system. For example, the term "soft output" may be used, because at this stage, any decision is possible. Indeed, the final decision could depend on post-processing of the soft outputs, for example. "Argmax" in FIG. 3 is an operator that indicates the sleep stage associated with the highest "soft output" (e.g., the highest probability).

For example, a useful property of neural networks is that they can produce probabilities associated with pre-defined sleep stages (e.g., Wake, REM, N1, N2, N3 sleep). Model component 32 (FIG. 1) is configured such that the set of probabilities constitute a so-called soft decision vector, which may be translated into a hard decision by determining which sleep stage is associated with a highest probability value (in a continuum of possible values) relative to other sleep stages. These soft decisions make it possible for system 10 to consider different possible sleep states on a continuum rather than being forced to decide which discrete sleep stage "bucket" particular EEG information fits into (as in prior art systems).

Returning to FIG. 1, model component 32 is configured such that both the values output from convolutional layers, and the soft decision value outputs, are vectors comprising continuous values as opposed to discrete values such as sleep stages. Consequently, convolutional and recurrent (soft decision) value outputs are available to be used by system 10 to modulate the intensity of the stimulation when the deep neural network detects decreases in a measure of wakefulness and/or stable sleep (e.g., a period of uninterrupted NREM or REM sleep) of the subject, as described herein, parameters determined (e.g., by information component 30 shown in FIG. 1) based on the raw sensor output signals (e.g., EEG signals) can be used to modulate stimulation intensity.

As described above, modulation component 36 is configured to cause sensory stimulator 16 to modulate an amount, timing, and/or intensity of the sensory stimulation. Modulation component 36 is configured to cause sensory stimulator to modulate the amount, timing, and/or intensity of the sensory stimulation based on the one or more brain activity and/or other parameters, values output from the convolutional and/or recurrent layers of the trained neural network, and/or other information. As an example, volume of auditory vibration, the strength of haptic vibration, the brightness of visual stimulation, and/or other stimulation intensities may be adjusted and/or otherwise controlled (e.g., modulated) based on value outputs from the deep neural network such as convolutional layer value outputs and recurrent layer value outputs (e.g., sleep stage (soft) prediction probabilities). In some embodiments, modulation component 36 is configured to cause one or more sensory stimulators 16 to modulate the intensity of the sensory stimulation responsive to an indication that subject 12 is experiencing one or more micro-arousals.

In some embodiments, modulation component 36 is configured to modulate the sensory stimulation based on the brain activity and/or other parameters alone, which may be determined based on the output signals from sensors 14 (e.g., based on a raw EEG signal). In these embodiments, the output of a deep neural network (and/or other machine learning models) continues to be used to detect sleep stages and/or stable sleep (e.g., as described above). However, the stimulation intensity may instead be modulated based on brain activity and/or other parameters or properties determined based on the sensor output signals. In some embodiments, the information in, or determined based on, the sensor output signals can also be combined with intermediate outputs of the network such as output of the convolution layers or the final outputs (soft stages) to modulate intensity (e.g., as described herein).

Figure 4:
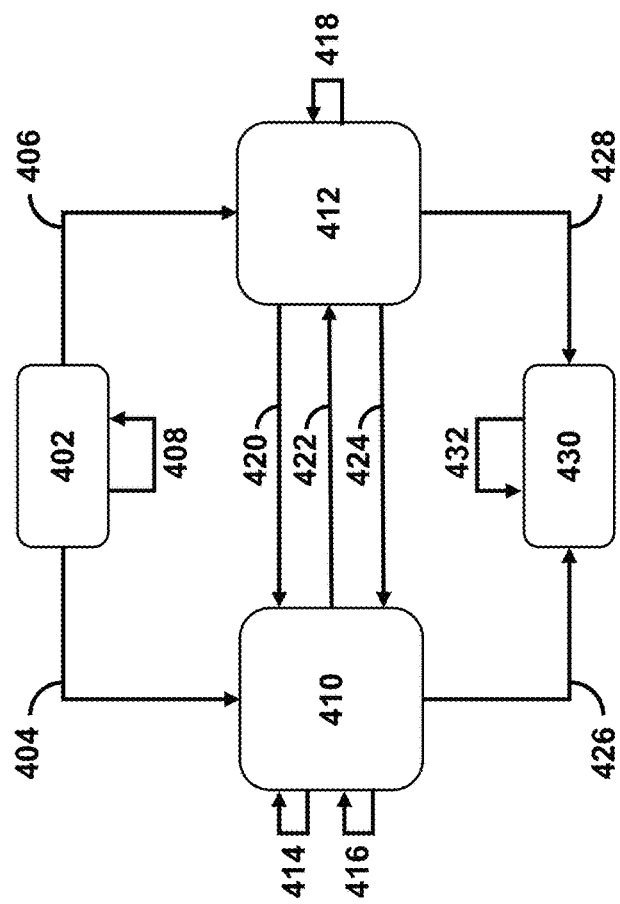
FIG. 4 illustrates an algorithm for controlling sensory stimulation delivered to a subject, in accordance with one or more embodiments.

FIG. 4 illustrates an algorithm 400 for controlling sensory stimulation delivered to a subject (e.g., 12, as shown in FIG. 1, and/or 202, as shown in FIG. 2) during a sleep session. As illustrated by algorithm 400 (which may be similar to and/or the same as system 10 shown in FIG. 1), the sensory stimulation may begin with an initial intensity state 402. In some embodiments, the initial intensity may be set by the subject. In some embodiments, the initial intensity may be preprogrammed. In some embodiments, the initial intensity may be personalized for the subject by the system (e.g., according to sleep history information, sleep architecture information, etc.). In some embodiments, if a noisy signal 408 is detected for the EEG signal (e.g., EEG signal 204, as shown in FIG. 2), algorithm 400 (e.g., controlled by modulation component 36 shown in FIG. 1) may remain in initial intensity state 402 until a clean signal is detected. In some embodiments, noisy signal 408 may be a signal having a noise level that breaches a threshold noise level. For example, a high noise level may correspond to a low-quality signal. Algorithm 400 may detect changes in the measure of wakefulness, i.e., the ratio between a high frequency (e.g., beta) portion of the EEG signal and a low frequency (e.g., theta) portion of the EEG signal (e.g., ratio 210, as shown in FIG. 2). In some embodiments, the measure of wakefulness is represented by the logarithm of this ratio, for example:

$$\text{Measure of wakefulness} = \log_{10}\left(\frac{\beta}{\theta}\right),$$

or any multiple thereof. An increase in this ratio indicates an increase in the measure of wakefulness, while a decrease in this ratio indicates a decrease in the measure of wakefulness.

In some embodiments, algorithm 400 may change between states in response to detecting a clean signal. In some embodiments, a clean signal may be a high-quality signal. In some embodiments, a clean signal may be a signal having a noise level that does not breach a noise level threshold. For example, higher levels of noise indicate lower-quality signals, so a clean signal may be one having a low noise level. In some embodiments, once a clean signal is detected, if an increasing measure of wakefulness 404 is detected, algorithm 400 (e.g., modulation component 36 shown in FIG. 1) may cause a transition from initial intensity state 402 to an intensity unchanged state 410. In some embodiments, once a clean signal is detected, if a decreasing measure of wakefulness 404 is detected, algorithm 400 may transition from initial intensity state 402 to an intensity decrease state 412. In some embodiments, increasing measure of wakefulness 404 and decreasing measure of wakefulness 406 are based upon raw EEG data and/or outputs from a deep neural network (e.g., as shown in FIG. 3). In some embodiments, increasing measure of wakefulness 404 and decreasing measure of wakefulness 406 indicate increases or decreases, respectively, in the ratio (e.g., 210, as shown in FIG. 2) between the high frequency portion of the EEG signals and the low frequency portion of the EEG signals of the subject.

In the intensity unchanged state 410, the one or more processors continue to deliver the sensory stimulation to the subject at a constant intensity. If noisy signals 414 (i.e., breaching a noise level threshold) are detected, algorithm 400 (e.g., modulation component 36 shown in FIG. 1) may cause the sensory stimulators to remain in intensity unchanged state 410. If micro-arousals 416 and/or other increases in wakefulness (e.g., increases of ratio 210, as shown in FIG. 2) are detected, algorithm 400 may cause the sensory stimulators (e.g., controlled by modulation component 36 shown in FIG. 1) to remain in intensity unchanged state 410. If a clean signal is detected which indicates a decreasing measure of wakefulness 422, algorithm 400 may cause the sensory stimulators (e.g., controlled by modulation component 36 shown in FIG. 1) to transition from intensity unchanged state 410 to an intensity decrease state 412. In intensity decrease state 412, sensory stimulators (e.g., controlled by modulation component 36 shown in FIG. 1) may modulate the intensity of the sensory stimulation delivered to the subject such that the intensity is based upon the measure of wakefulness. Thus, the intensity decrease state 412 may match the decreasing measure of wakefulness 418 (e.g., proportionally or otherwise related). For example, the intensity of the sensory stimulation may be modulated according to the following equations and/or other equations:

$$\rho = \log_{10}\left(\frac{\beta}{\theta}\right)$$

$$V(\rho) = V_i \times \left(1 + e^{\left(\frac{11 \times (\rho - \rho_{50})}{5 \times (\rho_{10} - \rho_{50})}\right)}\right)^{-1}$$

$$V(\rho_{50}) = \frac{V_i}{2}; V(\rho_{10}) = \frac{V_i}{10};$$

$$\frac{dV}{d\rho} = \frac{11 \times V^2}{5V_i \times (\rho_{50} - \rho_{10})} e^{\left(\frac{11 \times (\rho - \rho_{50})}{5 \times (\rho_{10} - \rho_{50})}\right)};$$

$$\Delta V = \lambda \times \Delta \rho \times \frac{dV}{d\rho};$$

where $\beta$ is the high frequency band of the EEG signal, $\theta$ is the low frequency band of the EEG signal, $V(\rho)$ is the intensity of the sensory stimulation, $V_i$ is an initial intensity (e.g., which may be set by the subject), $\rho$ is the measure of wakefulness, $\rho_{50}$ is the measure of wakefulness for which the intensity of the sensory stimulation is 50% of the initial intensity $V_i$, $\rho_{10}$ is the measure of wakefulness for which the intensity of the sensory stimulation is 10% of the initial intensity $V_i$, $$\frac{dV}{d\rho}$$

is the rate of change of the intensity function, $\Delta\rho$ is the difference between measures of wakefulness for two times, $\Delta V$ is the difference between intensities for two times, and $\lambda$ is a multiplicative constant. This example is not intended to be limiting, and the intensity of the stimulation may depend upon the measure of wakefulness in another way.

Figure 5:
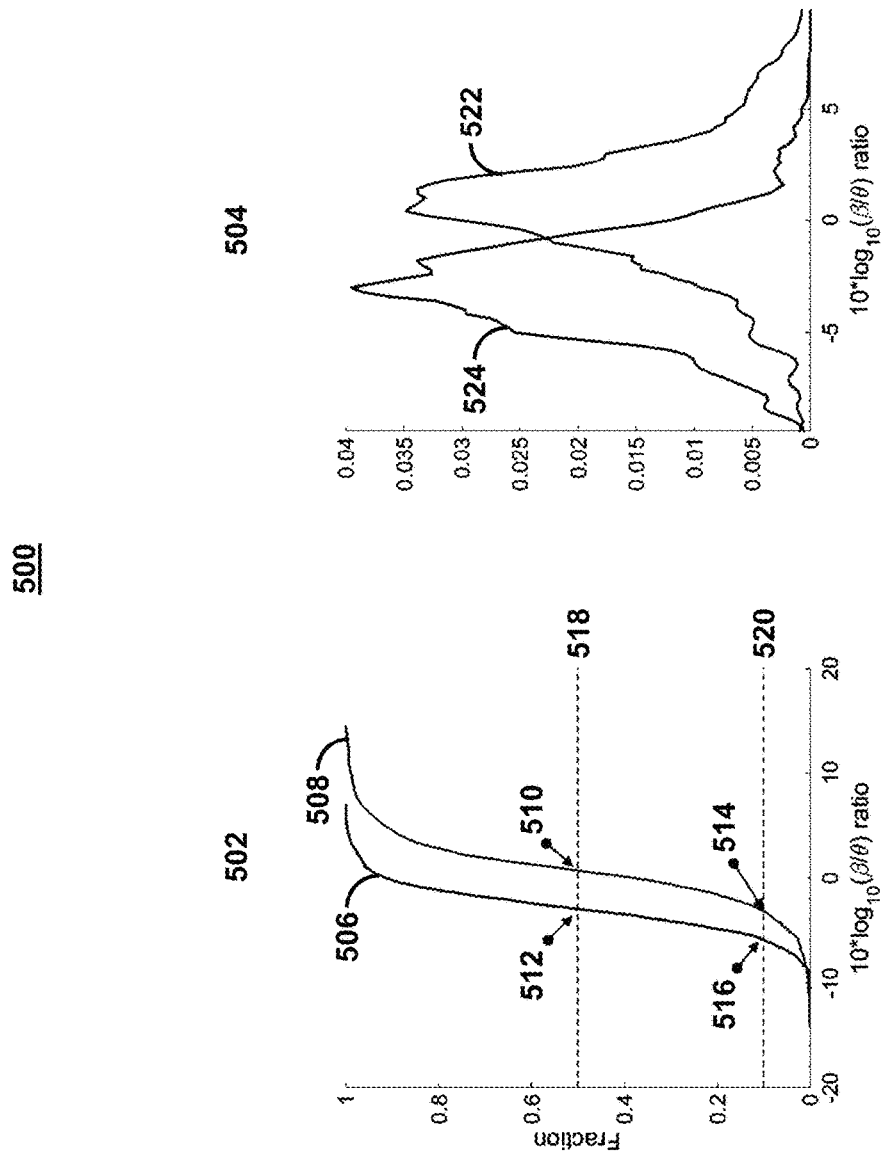
FIG. 5 illustrates a cumulative distribution function of a measure of wakefulness during a sleep session and a histogram of the measure of wakefulness during the sleep session, in accordance with one or more embodiments.

In some embodiments, the values of $\rho_{50}$ and $\rho_{10}$ may be obtained from a cumulative distribution function of $\rho$, as shown by data 500 in FIG. 5. Graph 502 shows a relationship between intensity and measure of wakefulness for a sleep session of a subject (e.g., 12, as shown in FIG. 1) during wake 506 and sleep 508. In graph 502, the vertical axis represents a fraction of the initial intensity (e.g., $V_i$) while the horizontal axis represents the measure of wakefulness (e.g., 10$\rho$). As the measure of wakefulness decreases, the fraction of the initial intensity likewise decreases (i.e., the intensity decreases as the measure of wakefulness decreases). The values of $\rho_{50}$ and $\rho_{10}$ are shown on graph 502 for the wake 506 and sleep 508 states. The $\rho_{50}$ values are shown where the wake 506 and sleep 508 states cross line 518 (which is positioned at 0.5). The $\rho_{50}$ values are represented by value 510 and value 512 for wake and sleep, respectively. The $\rho_{10}$ values are shown where the wake 506 and sleep 508 states cross line 520 (which is positioned at 0.1). The $\rho_{10}$ values are represented by value 514 and value 516 for wake and sleep, respectively. Graph 504 represents a histogram of the measure of wakefulness (e.g., 10$\rho$) for wake 522 and sleep 524. The histogram shows that the measure of wakefulness is higher during wake 522 than during sleep 524.

Returning to FIG. 4, in some embodiments, if the measure of wakefulness continues to decrease, algorithm 400 will remain in intensity decrease state 412. If a noisy signal 424 (i.e., breaching a noise level threshold) is detected, algorithm 400 may transition from intensity decrease state 412 to intensity unchanged state 410. If a clean signal (e.g., not breaching a noise level threshold) is detected (which indicates wake, a micro-arousal, and/or an increasing measure of wakefulness 420), algorithm 400 may transition to intensity unchanged state 410.

While algorithm 400 is in either intensity unchanged state 410 or intensity decrease state 412, the one or more sensors (e.g., 14, as shown in FIG. 1) may detect that the subject has entered stable sleep. In some embodiments, this determination may be based upon a clean EEG signal indicating stable sleep 426 or stable sleep 428. In some embodiments, the one or more processors may detect stable sleep based on the raw EEG signals and/or the outputs from a deep neural network (e.g., as shown in FIG. 3). In some embodiments, the measure of wakefulness (e.g., ratio 210, as shown in FIG. 2) may indicate that the subject has entered stable sleep. In some embodiments, algorithm 400 may require that the subject remains in stable sleep for a threshold amount of time (e.g., five minutes or another amount of time) before transitioning to another state.

Once a clean signal indicates stable sleep 426 or stable sleep 428 for the threshold amount of time, algorithm 400 may transition to intensity fade state 430. In intensity fade state 430, the one or more processors may cause an intensity of the modulated sensory stimulation to fade to zero (or to an intensity that is below a perceivability threshold). In some embodiments, the rate of decrease of the sensory stimulation in the intensity fade state 430 may be faster than the rate of decrease of the sensory stimulation in the intensity decrease state 412. For example, in some embodiments, the intensity of the sensory stimulation may decrease by two percent every six seconds in the intensity fade state 430. This example is not intended to be limiting, and any rate of decreasing intensity may be utilized. If a noisy signal 432 (i.e., breaching a noise level threshold) is detected while algorithm 400 is in intensity fade state 430, algorithm 400 may remain in intensity fade state 430.

Figure 6:
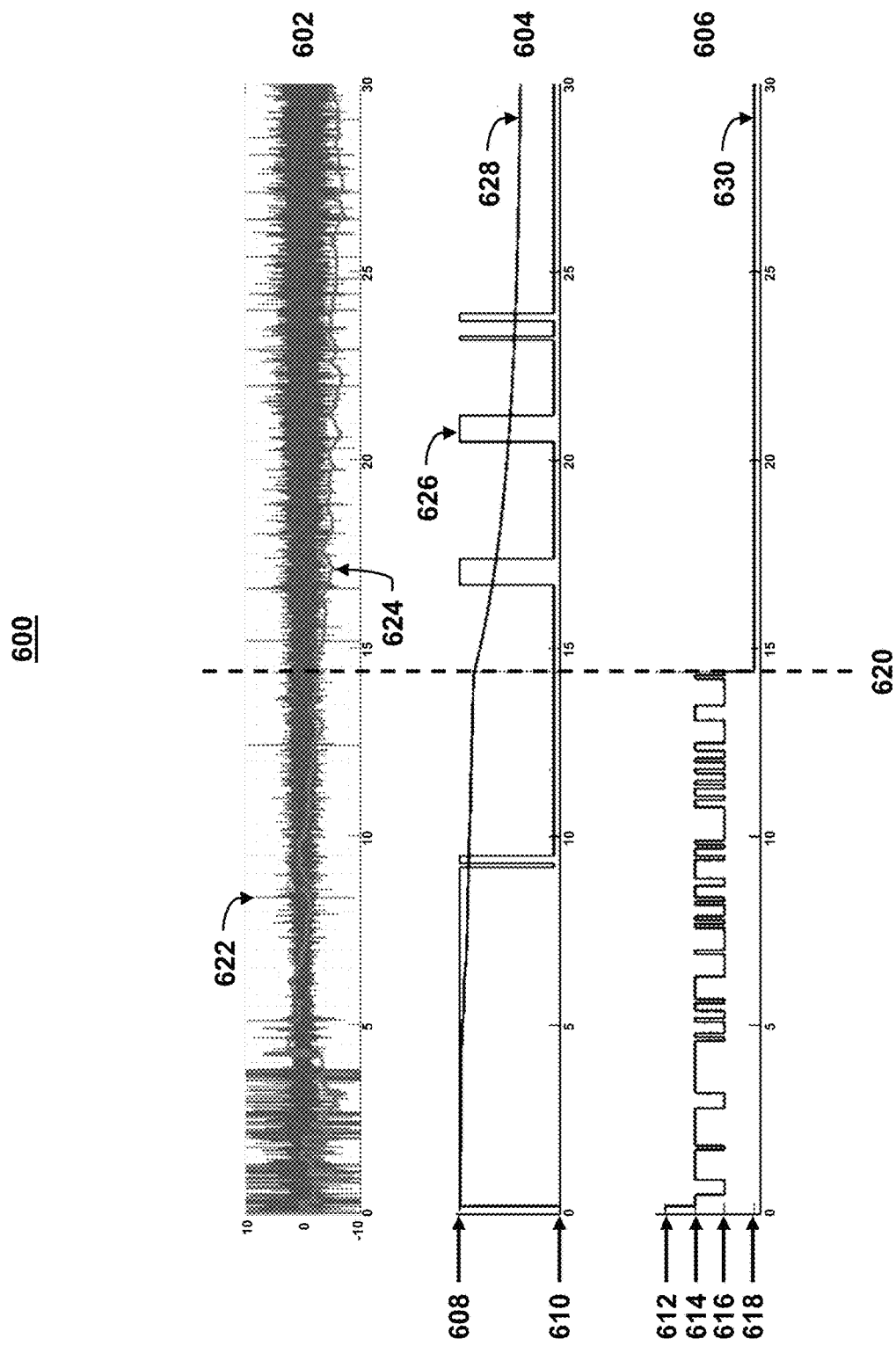
FIG. 6 illustrates operation of the algorithm for controlling sensory stimulation delivered to a subject, in accordance with one or more embodiments.

FIG. 6 illustrates operation 600 of algorithm 400 for controlling sensory stimulation delivered to a subject. Panel 602 shows an EEG signal 622 from a frontal location of a subject (e.g., 12, as shown in FIG. 1) during a wake to sleep transition. Panel 602 includes a measure of wakefulness 624

$$\left(\text{e.g., } \rho = 10 \log_{10} \frac{\beta}{\theta}\right).$$

Panel 604 shows a hypnogram 626 having two stages (wake 608 and sleep 610) and sensory stimulation intensity 628 over time. Panel 606 shows the state sequence 630 of the algorithm over time. In some embodiments, initial intensity 612 may correspond to initial intensity state 402 (i.e., as shown in FIG. 4), stable intensity 614 may correspond to intensity unchanged state 410 (i.e., as shown in FIG. 4), decreasing intensity 616 may correspond to intensity decrease state 412 (i.e., as shown in FIG. 4), and fading intensity 618 may correspond to intensity fade state 430 (i.e., as shown in FIG. 4). Panels 602, 604, and 606 align temporally, and stable sleep detection 620 occurs in each panel concurrently.

In panel 602, EEG signal 622 shows that the waves become higher in amplitude and lower in frequency with time (i.e., as the subject falls asleep). Measure of wakefulness 624 decreases with time, mirroring the changes in EEG signal 622 and indicating the progression of the wake to sleep transition. Measure of wakefulness 624 does not necessarily decrease monotonically. Panel 604 likewise displays the wake to sleep transition. In some embodiments, hypnogram 626 may be based upon raw EEG signals (e.g., EEG signal 622) and/or a deep neural network (e.g., as shown in FIG. 3) which determines sleep stages during a sleep session. Hypnogram 626 is in wake 608 for almost the first ten minutes of the sleep session. Once hypnogram 626 enters sleep 610 and remains in sleep 610 for a threshold amount of time (e.g., five minutes), the algorithm identifies the subject as being in stable sleep. Therefore, stable sleep detection 620 occurs approximately five minutes after hypnogram 626 enters a stable period of sleep 610. Although hypnogram enters wake 608 periodically after stable sleep detection 620 occurs (e.g., micro arousals), state sequence 630 remains in fading intensity 618 for the duration of the sleep session shown in FIG. 6.

Panel 606 shows how state sequence 630 reacts to changes in the measure of wakefulness 624 over time. After state sequence 630 leaves initial intensity 612 but before stable sleep detection 620 occurs, state sequence 630 alternates between stable intensity 614 and decreasing intensity 616. Periods of stable intensity 614 correspond to increases or lack of change in measure of wakefulness 624. Periods of decreasing intensity 616 correspond to decreases in measure of wakefulness 624.

The position of state sequence 630 at initial intensity 612 corresponds to an initial intensity level of sensory stimulation intensity 628. Following the period of initial intensity 612, periods of stable intensity 614 cause sensory stimulation intensity 628 to remain at a constant level, while periods of decreasing intensity 616 cause sensory stimulation intensity 628 to decrease. Because of the alternation between stable intensity 614 and decreasing intensity 616, sensory stimulation intensity 628 may decrease monotonically with time. The overall rate of decrease of sensory stimulation intensity 628 before stable sleep detection 620 is smaller than the rate of decrease of sensory stimulation intensity 628 after stable sleep detection 620. Once stable sleep detection 620 occurs, state sequence 630 enters fading intensity 618. Fading intensity 618 causes sensory stimulation intensity 628 to decrease at a faster rate. In some embodiments, sensory stimulation intensity 628 may decrease at a constant rate. In some embodiments, as shown in FIG. 6, sensory stimulation intensity 628 may decrease at a varying rate. In some embodiments, sensory stimulation intensity 628 may decrease at a certain rate until it falls below a perceivability threshold, at which point sensory stimulation intensity 628 may fall to zero.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via subject interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

Subject interface 24 is configured to provide an interface between system 10 and subject 12, and/or other subjects through which subject 12 and/or other subjects may provide information to and receive information from system 10. This enables data, cues, results, and/or instructions and any other communicable items, collectively referred to as "information," to be communicated between a subject (e.g., subject 12) and one or more of sensor 14, sensory stimulator 16, external resources 18, processor 20, and/or other components of system 10. For example, a hypnogram, EEG data, NREM or REM sleep stage probability, and/or other information may be displayed for subject 12 or other subjects via subject interface 24. As another example, subject interface 24 may be and/or be included in a computing device such as a desktop computer, a laptop computer, a smartphone, a tablet computer, and/or other computing devices. Such computing devices may run one or more electronic applications having graphical subject interfaces configured to provide information to and/or receive information from subjects.

Examples of interface devices suitable for inclusion in subject interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, subject interface 24 comprises a plurality of separate interfaces. In some embodiments, subject interface 24 comprises at least one interface that is provided integrally with processor 20 and/or other components of system 10. In some embodiments, subject interface 24 is configured to communicate wirelessly with processor 20 and/or other components of system 10.

It is to be understood that other communication techniques, either hard-wired or wireless, are also contemplated by the present disclosure as subject interface 24. For example, the present disclosure contemplates that subject interface 24 may be integrated with a removable storage interface provided by electronic storage 22. In this example, information may be loaded into system 10 from removable storage (e.g., a smart card, a flash drive, a removable disk, etc.) that enables the subject(s) to customize the implementation of system 10. Other exemplary input devices and techniques adapted for use with system 10 as subject interface 24 comprise, but are not limited to, an RS-232 port, RF link, an IR link, modem (telephone, cable or other). In short, any technique for communicating information with system 10 is contemplated by the present disclosure as subject interface 24.

Figure 7:
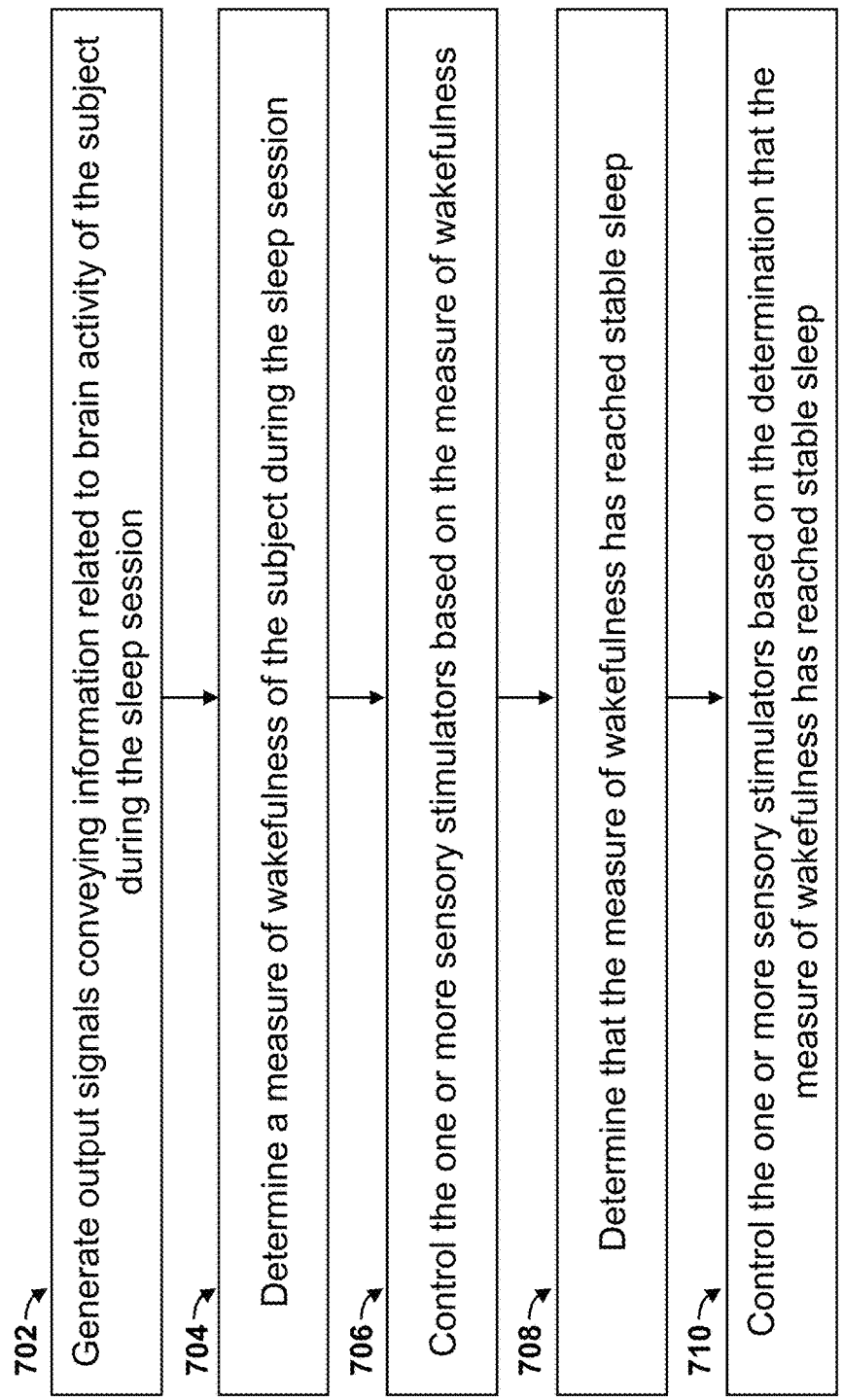
FIG. 7 illustrates a method for controlling sensory stimulation delivered to a subject during a sleep session, in accordance with one or more embodiments.

FIG. 7 illustrates method 700 for controlling sensory stimulation delivered to a subject during a sleep session. The system comprises one or more sensors, one or more sensory stimulators, one or more processors configured by machine-readable instructions, and/or other components. The one or more processors are configured to execute computer program components. The computer program components comprise an information component, a model component, a control component, a modulation component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to brain activity of the subject during the sleep session are generated. The output signals are generated during a sleep session of the subject and/or at other times. In some embodiments, operation 702 is performed by sensors the same as or similar to sensors 14 (shown in FIG. 1 and described herein).

In some embodiments, operation 702 includes providing the information in the output signals to the neural network in temporal sets that correspond to individual periods of time during the sleep session. In some embodiments, operation 710 includes causing the trained neural network to output the detected NREM or REM sleep for the subject during the sleep session based on the temporal sets of information. In some embodiments, operation 702 is performed by a processor component the same as or similar to model component 32 (shown in FIG. 1 and described herein).

At an operation 704, a measure of wakefulness of the subject during the sleep session is determined. In some embodiments, the measure of wakefulness may comprise a ratio of a high frequency portion of the EEG signals (e.g., beta signals) to a low frequency portion of the EEG signals (e.g., theta signals). In some embodiments, the measure of wakefulness may comprise a power ratio of a power associated with a high frequency portion of the brain signals to a power associated with a low frequency portion of the brain signals. In some embodiments, the measure of wakefulness may comprise a logarithm of the ratio of high to low frequency EEG signals. In some embodiments, the measure of wakefulness may indicate a sleep stage of the subject (e.g., wake, REM, N1, N2, N3 sleep, etc.). In some embodiments, operation 704 is performed by a processor component the same as or similar to control component 34 (shown in FIG. 1 and described herein).

At an operation 706, the one or more sensory stimulators are controlled based on the measure of wakefulness (e.g., as determined at operation 704). In some embodiments, the one or more sensory stimulators may deliver modulated sensory stimulation (e.g., with a varying intensity) to the subject. In some embodiments, modulation of the sensory stimulation may correspond to changes in the measure of wakefulness (e.g., as described in relation to FIGS. 4 and 6). For example, an increase or lack of change in the measure of wakefulness may cause the one or more sensory stimulators to deliver sensory stimulation to the subject at a constant intensity. A decrease in the measure of wakefulness may cause the one or more sensory stimulators to decrease the intensity of the sensory stimulation delivered to the subject. In some embodiments, operation 706 is performed by a processor component the same as or similar to control component 34 (shown in FIG. 1 and described herein).

At an operation 708, it is determined that the measure of wakefulness has reached stable sleep. In some embodiments, stable sleep may comprise non-rapid eye movement (NREM) sleep (which includes stages N1, N2 and N3 or S1 to S4 according to the old nomenclature) or rapid eye movement (REM) sleep. In some embodiments, a subject may remain in uninterrupted NREM or REM sleep for a threshold period of time before stable sleep is determined. In some embodiments, operation 708 is performed by a processor component the same as or similar to control component 34 (shown in FIG. 1 and described herein).

At an operation 710, the one or more sensory stimulators are controlled based on the determination that the measure of wakefulness has reached stable sleep. In some embodiments, the one or more sensory stimulators may decrease the intensity of the sensory stimulation delivered to the subject at a faster rate once stable sleep is detected. In some embodiments, operation 710 is performed by a processor component the same as or similar to control component 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for controlling sensory stimulation delivered to a subject during a sleep session, the system comprising:

one or more sensors configured to generate output signals conveying information related to brain activity of the subject during the sleep session;
one or more sensory stimulators configured to provide sensory stimulation to the subject; and
one or more processors coupled to the one or more sensors and the one or more sensory stimulators, the one or more processors configured by machine-readable instructions to:
determine, based on the output signals, a measure of wakefulness of the subject during the sleep session;
control the one or more sensory stimulators based on the measure of wakefulness;
determine, based on the output signals, that the measure of wakefulness has reached stable sleep; and
control the one or more sensory stimulators based on the determination that the measure of wakefulness has reached stable sleep,
wherein the one or more processors are further configured to determine that the output signals comprise a noise level that breaches a threshold noise level, and
wherein, to control the one or more sensory stimulators based on the determination that the output signals comprise the noise level that breaches the threshold noise level, the one or more processors are further configured to cause the one or more sensory stimulators to deliver the sensory stimulation to the subject at a constant intensity.

2. The system of claim 1, wherein the measure of wakefulness comprises a ratio between a high frequency portion of the output signals and a low frequency portion of the output signals.

3. The system of claim 1, wherein the measure of wakefulness comprises a power ratio between a power associated with a high frequency portion of the output signals and a power associated with a low frequency portion of the output signals.

4. The system of claim 1, wherein, to control the one or more sensory stimulators based on the measure of wakefulness, the one or more processors are further configured to:
detect a decrease in the measure of wakefulness based on the output signals; and
cause the one or more sensory stimulators to decrease an intensity of the sensory stimulation delivered to the subject based on the detected decrease in the measure of wakefulness.

5. The system of claim 1, wherein, to control the one or more sensory stimulators based on the measure of wakefulness, the one or more processors are further configured to:
detect an increase in the measure of wakefulness based on the output signals; and
cause the one or more sensory stimulators to deliver the sensory stimulation to the subject at a constant intensity based on the detected increase in the measure of wakefulness.

6. The system of claim 1, wherein, to control the one or more sensory stimulators based on the determination that the measure of wakefulness has reached stable sleep, the one or more processors are further configured to decrease an intensity of the sensory stimulation at a faster rate than at higher measures of wakefulness.

7. The system of claim 1, wherein the one or more sensors comprise one or more electroencephalogram (EEG) electrodes configured to generate the information related to brain activity.

8. The system of claim 1, wherein the sensory stimulation comprises auditory vibrations, haptic vibrations, or light pulses.

9. A method for controlling sensory stimulation delivered to a subject during a sleep session with a system, the system comprising one or more sensors, one or more sensory stimulators, and one or more processors, the method comprising:
generating, with the one or more sensors, output signals conveying information related to brain activity of the subject during the sleep session;
determining, with the one or more processors, a measure of wakefulness of the subject during the sleep session based on the output signals;
controlling, with the one or more processors, the one or more sensory stimulators based on the measure of wakefulness;
determining, with the one or more processors, that the measure of wakefulness has reached stable sleep based on the output signals;
controlling, with the one or more processors, the one or more sensory stimulators based on the determination that the measure of wakefulness has reached stable sleep; and
determining that the output signals comprise a noise level that breaches a threshold noise level,
wherein controlling the one or more sensory stimulators based on the determination that the output signals comprise the noise level that breaches the threshold noise level comprises causing the one or more sensory stimulators to deliver the sensory stimulation to the subject at a constant intensity.

10. The method of claim 9, wherein the measure of wakefulness comprises a ratio between a high frequency portion of the output signals and a low frequency portion of the output signals.

11. The method of claim 9, wherein the measure of wakefulness comprises a power ratio between a power associated with a high frequency portion of the output signals and a power associated with a low frequency portion of the output signals.

12. The method of claim 9, wherein controlling, with the one or more processors, the one or more sensory stimulators based on the measure of wakefulness comprises:
detecting, with the one or more processors, a decrease in the measure of wakefulness based on the output signals; and
causing, with the one or more processors, the one or more sensory stimulators to decrease an intensity of the sensory stimulation delivered to the subject based on the detected decrease in the measure of wakefulness.

13. The method of claim 9, wherein controlling, with the one or more processors, the one or more sensory stimulators based on the measure of wakefulness comprises:
detecting, with the one or more processors, an increase in the measure of wakefulness based on the output signals; and
causing, with the one or more processors, the one or more sensory stimulators to deliver the sensory stimulation to the subject at a constant intensity based on the detected increase in the measure of wakefulness.

14. The method of claim 9, wherein controlling the one or more sensory stimulators based on the determination that the measure of wakefulness has reached stable sleep comprises decreasing an intensity of the sensory stimulation at a faster rate than at higher measures of wakefulness.

15. The method of claim 9, wherein the one or more sensors comprise one or more electroencephalogram (EEG) electrodes configured to generate the information related to brain activity.

16. The method of claim 9, wherein the sensory stimulation comprises auditory vibrations, haptic vibrations, or light pulses.

* * * * *